(12) United States Patent
Koning et al.

(10) Patent No.: US 10,189,783 B2
(45) Date of Patent: Jan. 29, 2019

(54) POLYFUNCTIONAL COMPOUNDS

(71) Applicant: DSM IP Assets B.V., Heerlen (NL)

(72) Inventors: Cornelis Eme Koning, Echt (NL); Paulus Franciscus Anna Buijsen, Echt (NL); Adrianus Jozephus Hendricus Lansbergen, Echt (NL); Alwin Papegaaij, Echt (NL); Douglas Hayden, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/535,832

(22) PCT Filed: Dec. 21, 2015

(86) PCT No.: PCT/EP2015/080748
§ 371 (c)(1),
(2) Date: Jun. 14, 2017

(87) PCT Pub. No.: WO2016/097403
PCT Pub. Date: Jun. 23, 2016

(65) Prior Publication Data
US 2017/0355672 A1    Dec. 14, 2017

(30) Foreign Application Priority Data

Dec. 19, 2014   (EP) .................................... 14199363

(51) Int. Cl.
*C08G 63/685* (2006.01)
*C09D 167/06* (2006.01)
(Continued)

(52) U.S. Cl.
CPC ....... *C07D 209/48* (2013.01); *C07D 207/404* (2013.01); *C08G 63/48* (2013.01);
(Continued)

(58) Field of Classification Search
CPC ... C09D 167/06; C08G 63/685; C07D 207/46
See application file for complete search history.

(56) References Cited

U.S. PATENT DOCUMENTS 3,960,799 A     6/1976  Mosimann et al.
4,296,122 A *  10/1981  Cragoe, Jr. ............. C07C 37/18
                                                                    514/469
(Continued)

FOREIGN PATENT DOCUMENTS

JP          1-207362         8/1989
WO    WO 2008/101722     8/2008
WO    WO 2014/044732     3/2014

OTHER PUBLICATIONS

International Search Report for PCT/EP2015/080748, dated Mar. 2, 2016, 2 pages.
(Continued)

*Primary Examiner* — Tae H Yoon
(74) *Attorney, Agent, or Firm* — Nixon & Vanderhye P.C.

(57) ABSTRACT

The present invention relates to a an imide compound according to anyone of formulas Ia, Ib, Ic, or Ie wherein R1 is H or a C1-C20 optionally substituted hydrocarbon group; both R2 and R5 are a COOH group or one of R2 and R5 is a COOH group while the other substituent is H, methyl or ethyl group; R3 and R4 are independently H, or C1-C20 optionally substituted hydrocarbon group; R6 is H or a methyl group; R7 and R8 are independently H, methyl or ethyl.

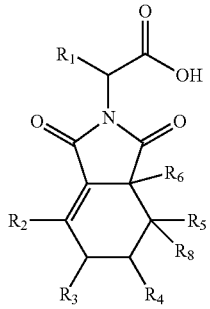

Ia

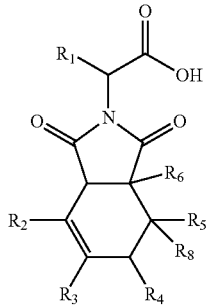

Ib

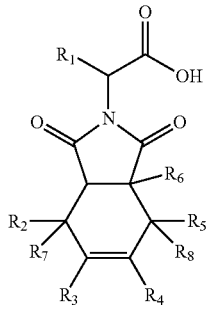

Ic (Continued)

-continued

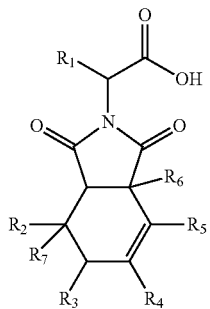

Id

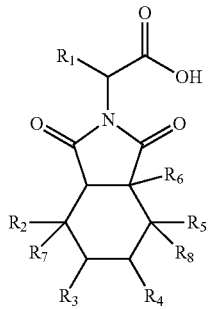

Ie

(51) Int. Cl.
 *C07D 207/46*  (2006.01)
 *C07D 209/48*  (2006.01)
 *C07D 207/404*  (2006.01)
 *C08G 63/48*  (2006.01)
 *C09D 167/08*  (2006.01)
 *C09D 5/03*  (2006.01)

(52) U.S. Cl.
 CPC ............ *C08G 63/685* (2013.01); *C09D 5/03* (2013.01); *C09D 167/08* (2013.01)

(56)       References Cited

U.S. PATENT DOCUMENTS 4,663,424 A * 5/1987 Stix ................. C08G 63/6858
                522/104
2002/0122947 A1 * 9/2002 Berg ................. C09D 167/08
                428/447

OTHER PUBLICATIONS

Written Opinion of the ISA for PCT/EP2015/080748, dated Mar. 2, 2016, 5 pages.
International Preliminary Report on Patentability for PCT/EP2015/080748, dated Mar. 13, 2017, 52 pages.

21 Claims, No Drawings

* cited by examiner

POLYFUNCTIONAL COMPOUNDS

This application is the U.S. national phase of International Application No. PCT/EP2015/080748 filed 21 Dec. 2015, which designated the U.S. and claims priority to EP Patent Application No. 14199363.4 filed 19 Dec. 2014, the entire contents of each of which are hereby incorporated by reference.

The present invention relates to specific imides, resins prepared from said imides, compositions comprising said resins, coatings prepared from said compositions and articles coated with said coatings.

Alkyd resins and powder coating resins are known in the art. Many publications exist that describe the resin compositions and the compounds used to prepare the resin compositions.

WO 2008/101722 A1 describes grafted autooxidisable polyester resins, wherein the resin is prepared by grafting of at least a diacid or its anhydride onto a first agent by a Diels-Alder and/or Ene reaction, followed by a reaction with a second agent. A disadvantage of the resin composition of WO2008/101722 is the slow drying, and sometimes yellowing of the product. U.S. Pat. No. 3,960,799 A, WO 2014/044732 A1 WO 2008/101722 A1, and JP H01 207362 A do not disclose imide compounds, and do not disclose compositions thereof, as the imide compounds and compositions thereof are claimed herein.

In general, paints (such as alkyd paints and powder coatings) for professional and do-it-yourself applications are subject to increasing technical and ecological restrictions. Emissions of volatile organic compounds (VOC) must be reduced to protect the environment. Polyester resins with a high content of solids and/or which are water borne (such as alkyd resins) have been used to address the problem of VOC. Nowadays, it is also desirable that paints are obtained from sustainable sources. It is therefore a preferred object of the invention that the resins have a high biorenewable content as defined herein.

The invention relates to an imide compound according to anyone of formulas Ia, Ib, Ic, Id or Ie

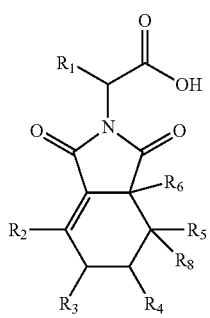

Ia

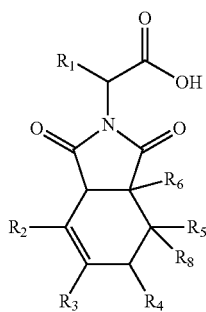

Ib

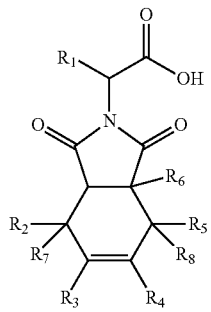

Ic

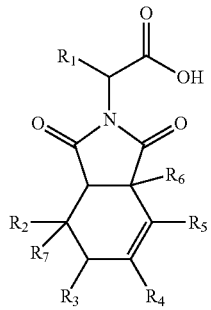

Id

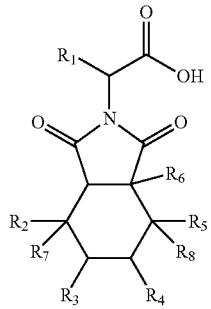

Ie wherein R1 is H or a C1-C20 optionally substituted hydrocarbon group;
both R2 and R5 are a COOH group or one of R2 and R5 is a COOH group while the other substituent is H, methyl or ethyl group;
R3 and R4 are independently H, or C1-C20 optionally substituted hydrocarbon group;
R6 is H or a methyl group;
R7 and R8 are independently H, methyl or ethyl.

The compounds according to the invention can be obtained in a high yield under mild reaction conditions. The compounds can be beneficially used in alkyd resin compositions, powder paint compositions, polyester resins and polyurethane resins and coatings, like for example can & coil coatings, and show interesting paint properties, like fast drying, high hardness and low yellowing. This makes the new biobased materials even more attractive, since in addition to the environmental friendly and sustainable nature of the compounds according to the present invention, also improved properties can be obtained.

The compounds according to formulas Ia-d are maleimide based Diels Alder adducts (R6=H), or preferably citraconimide based Diels Alder adducts (R6=methyl). The compound according to formula Ie is the hydrogenated Diels Alder adduct of the compound as defined in anyone of formulas Ia-Id.

An imide group is a functional group consisting of two acyl groups bound to nitrogen.

The compounds according to formulas Ia-Id can be up to 100% biobased in case the imide is formed by reacting maleic acid or citraconic acid, or their anhydrides maleic anhydride or citraconic anhydride, with an aminoacid to yield maleimide or citraconimide compounds, which can be reacted with a conjugated diene to render the compounds according to formula Ia-d, and optionally hydrogenated to the compound according to formula Ie.

Surprisingly the compounds Ia-e can be obtained in a high yield.

In a preferred embodiment R6 is a methyl group, such that the compounds are citraconimide based Diels-Alder adducts.

R1 can be H or a C1-C20 optionally substituted hydrocarbon group. Preferably the N—C(R1)-COOH fragment stems from an aminoacid which has been reacted with maleic acid, citraconic acid, or their anhydrides. Examples of R1 are H, methyl, hydroxymethyl, 1-hydroxyethyl, isopropyl, sec-butyl, 2-methyl-propyl, 2(methylthio)ethyl, benzyl, tolyl, parahydroxytolyl, or any other organic fragment from aminoacids such as for example arginine, histidine, lysine, aspartic acid, glutamic acid, serine, threonine, asparagine, glutamine, cysteine, selenocysteine, glycine, proline, alanine, valine, isoleucine, methionine, phenylalanine, tyrosine and tryptophan. More preferably R1 is H or a C1-C20 hydrocarbon group, Preferred examples of C1-C20 hydrocarbon groups are methyl, isopropyl, sec-butyl, 2-methyl-propyl, benzyl and tolyl. Most preferred examples are H and benzyl.

The compounds Ia, Ib, Ic, Id and Ie comprise at least two COOH groups, one of these always being the COOH group already drawn in structures Ia-Ie and being connected to R1 via one carbon atom. R2 and R5 are both a COOH group or one of R2 and R5 is a COOH group. In a preferred embodiment, one of R2 and R5 is a COOH group, while the other substituent is H, methyl or ethyl group, more preferably the other substituent is methyl.

R3 and R4 are independently H, or C1-C20 optionally substituted hydrocarbon group. In case R3 and/or R4 is a substituted C1-C20 hydrocarbon group, preferred substituents are selected from hydroxyl and carboxyl group. R3 and R4 can form a fused ring, for example a cyclic structure like a 5-membered or 6-membered ring structure. Preferably R3 and R4 are H.

R7 and R8 independently are chosen from H, methyl or ethyl. Preferably R7 and R8 are both H.

The compounds Ia, Ib, Ic, and Id are isomers: the main difference between the compounds is the position of the double bond which resides after completion of the Diels Alder reaction of the maleimide or citraconimide with the conjugated diene. This double bond may take different positions, so that in most cases a mixture of isomeric products is obtained after reacting the maleimide or citraconimide with the conjugated diene.

The compound according to formulas Ia-d can be prepared with a method comprising the steps of
a) Providing maleic anhydride or citraconic anhydride (formula II), or maleic acid or citraconic acid;
b) Reacting said acid or anhydride with a primary amine according to formula III to obtain a maleimide or citraconimide according to formula IV,
c) Reacting the product according to formula IV with a conjugated diene according to formula V in a Diels Alder reaction to obtain anyone of the compounds as defined in formulas Ia, Ib, Ic or Id, wherein R1, R2, R3, R4, R5, R6, R7 and R8 are the same as defined above.

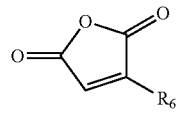

II

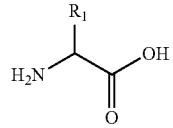

III

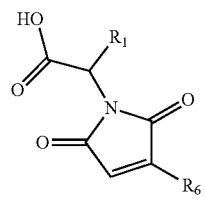

IV

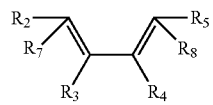

V

Alternatively the compound according to formulas Ia-d can be prepared with a method comprising the steps of
a) Providing maleic anhydride or citraconic anhydride (formula II), or maleic acid or citraconic acid;
b) Reacting said acid or anhydride with a conjugated diene according to formula V in a Diels Alder reaction to obtain an adduct,
c) Reacting the Diels Alder adduct with a primary amine according to formula III to obtain anyone of the compounds as defined in formulas Ia, Ib, Ic or Id,
wherein R1, R2, R3, R4, R5, R6, R7 and R8 are the same as defined above.

Examples of dienes are rosin, conjugated fatty acids, sorbic acid and muconic acid. Preferred examples of dienes are sorbic acid and muconic acid.

Optionally it may be desirable to protect the double bond of maleic anhydride during the imidization reaction. After imidization the protection can be removed to perform the Diels Alder reaction of the maleimide.

The preparation of the adduct used in the present invention may be carried out in the conventional manner for Diels Alder additions by heating the reaction mixture, the reactants being present in substantially stoichiometric proportions or with excess of diene and optionally in a suitable organic solvent, if required for fluidity. A Diels Alder catalyst, e.g. a Lewis acid such as aluminum chloride may be employed, however un-catalyzed reactions are preferred. The reaction temperature is preferably higher than 50° C., more preferably higher than 70° C. and preferably lower than the decomposition temperature of the product. The elevated temperature is maintained for a sufficient time to obtain an acceptable yield of the adduct. The time required depends on the reactivity of the particular reagents, the temperature, the stability of the product and commercial considerations (e.g. the value of the product against the cost of prolonging the heating step), however, typically, it is greater than 30 minutes, preferably greater than one hour, more preferably greater than two hours. The preparation of the adduct used in the present invention can be effected with raised pressure as well as without raised pressure. The preparation of the adduct based on volatile reactant is preferably effected with raised pressure. The preparation of the adduct used in the present invention is preferably effected in the presence of a polymerization inhibitor, for example hydroquinone.

The invention also relates to a resin composition comprising anyone of the above mentioned compounds Ia, Ib, Ic, Id or Ie, and its preferred embodiments. As used herein, a resin composition is the composition of compounds used to prepare a resin.

The invention further relates to an alkyd resin composition comprising anyone of the above mentioned compounds Ia, Ib, Ic, Id or Ie, and its preferred embodiments.

Prior art alkyd resins are typically obtained from a polycondensation of fatty acids or vegetable oils (30 to 70% by weight), polyols such as glycerol or pentaerythritol (10 to 40% by weight) and polyacids such as phthalic anhydride (10 to 40% by weight). These known alkyd resins have a broad molecular weight distribution and a branched structure, contain residual hydroxyl and carboxyl groups for wetting properties and are capable of autoxidative drying. Due to auto-oxidization, alkyd resins discolor in the dark and turn yellow. This tendency is even more pronounced for renewable alkyds that contain rosin and a high proportion of fatty acid. It is therefore desirable to find alkyd resins having improved properties.

As used herein unsaturated alkyd resin (for convenience also abbreviated herein to "alkyd resin") denotes a polyester comprising one or more unsaturated fatty acid moieties which are auto-oxidizable in air under standard conditions.

The alkyd resin composition (the composition of compounds used to prepare the alkyd resin) comprises
  a. 1-60 wt % of a compound according to formulas Ia, Ib, Ic, Id or Ie;
  b. 10-40 wt % of an alcohol having a number average hydroxy functionality≥2.0;
  c. 30-70 wt % of fatty acids and/or vegetable oils;
  d. 0-50 wt % of a mono and/or polyfunctional compound capable of esterification (such as for example those containing OH and/or COOH groups), which compound is different from the compounds used in a, b and c;
wherein the wt % is determined based on the total of weight of compounds a, b, c and d.

The compounds according to formulas Ia, Ib, Ic, Id or Ie may be present in the alkyd resin compositions in an amount of at least 1 wt-% and more preferably at least 5 or 10 wt-%, based on the total of weight of compounds a, b, c and d. Conveniently the compounds may be present in the alkyd resin compositions in an amount of less than 60 wt-% more conveniently less than 50 wt-%.

The compounds according to formulas Ia, Ib, Ic, Id or Ie may be present in the alkyd resin compositions in an amount of from 1 to 60 wt-%, preferably from 5 to 50 wt-%, more preferably from 10 to 40 wt-%. based on the total of weight of compounds a, b, c and d.

Alcohol (Compound b)

The alkyd resin composition also comprises 10-40 wt % (based on the total of weight of compounds a, b, c and d) of an alcohol having a number average hydroxy functionality ≥2.0.

Suitable alcohols may in principle be any hydroxy (i.e. OH group) functional compound or mixture of hydroxy functional compounds with a number average hydroxy functionality ≥2.0. By number average hydroxyl functionality is herein meant to take into account that even though an individual alcohol molecule has a discrete number of hydroxy groups, mixtures of alcohols typically will have a non-discrete medium hydroxy functionality. For example, one molecule may have a hydroxy functionality of 1 and another molecule may have a hydroxy functionality of 3. This will lead to a number average hydroxy functionality of 2.

In a preferred embodiment, the alcohol has a number average hydroxy functionality ≥2.5, even more preferred ≥2.8 and most preferred ≥3.

In a preferred embodiment, the alcohol has a number average hydroxy functionality of <15, preferably <10, more preferably <8, even more preferably <6, even more preferably <4.5, as this will allow for at least some of the polyol to participate in crosslinking with neighboring or the same polymer molecule.

The alcohol may comprise aliphatic parts and/or aromatic parts dependent on the required properties of the alkyd resin. The alcohol may comprise other functional groups, such as for example one or more acid groups, amine groups, urea groups, ester groups, unsaturations etc. However, it is preferred that the alcohol has only limited number of other functional groups. Particularly, it was found to be advantageous to have the amine number average functionality below about 0.2 since this reduced the yellowing considerably. It is preferred that the alcohol has only a limited number of other functional groups.

The term alcohol designates herein both individual (pure) alcohols as well as mixtures of alcohols unless otherwise stated. The individual alcohols preferably have a functionality of at least 2 to ensure that the alcohol does not act as an endcap group. The alcohol may be a mixture of several alcohols with the same or varying functionality (hydroxy and/or other functional groups).

In a preferred embodiment, at least 50 weight % of the alcohol has a hydroxy functionality ≥3, more preferably ≥4. More preferably at least 50 weight % of the alcohol has three functional groups, even more preferably at least 50 weight % of the alcohol has four functional groups. Particularly, it was found to be advantageous to utilize an alcohol, wherein at least 80 weight % of the alcohol has a hydroxy functionality ≥3, more preferably ≥4. More preferably at least 80 weight % of the alcohol has three functional groups. In a particularly preferred embodiment, the functionality of the alcohol has substantially solely hydroxy functionality, such as at least 90 weight % of the alcohol has hydroxy functionality, or the alcohol has solely (i.e. 100 weight %) hydroxy functionality.

Preferably at least 50 weight % of the alcohol is selected from the group consisting of glycerol, trimethylol propane, pentaerythritol, di-pentaerythritol, tri-pentaerythritol, isosorbide, isoidide, isomannide, hydrogenated bisphenol A, ethylene glycol, propylene glycol, poly ethylene glycol, di ethylene glycol, neo pentyl glycol, 2,3 butanediol, sugars like for example cellulose, sucrose, sorbitol, fructose and alike, polyglycerols having from 2 to 10 OH groups and mixtures thereof. In a highly preferred embodiment, the alcohol consists substantially of one or more alcohols selected from the group consisting of glycerol, trimethylol propane, pentaerythritol, isosorbide, isoidide, isomannide, hydrogenated bisphenol A, ethylene glycol, propylene glycol, polyethyleneglycol, diethylene glycol, neo pentyl glycol, 2,3 butanediol and sorbitol. By consisting substantially of is here meant that nearly all of the alcohol, such as more than 90 weight %, more than 95 weight % or more than 98 weight % of the alcohol is selected from the group consisting of glycerol, trimethylol propane, pentaerythritol, isoidide, isomannide, isosorbide, hydrogenated bisphenol A, ethylene glycol, 1.2-propylene glycol, 1.3-propylenglycol, polyethyleneglycol, diethyleneglycol, neopentylglycol, 2,3 butanediol and sorbitol. In a highly preferred embodiment, the alcohol consists of one or more alcohols selected from the group consisting of glycerol, trimethylol propane, pentaerythritol, isosorbide, isoidide, isomannide, hydrogenated bisphenol A, ethylene glycol, propylene glycol, polyethyleneglycol, diethylene glycol, neo pentyl glycol, 2,3 butanediol and sorbitol.

In a preferred embodiment, at least 50 weight % of the alcohol has a hydroxy functionality ≥3, more preferably ≥4.

Particularly preferred alcohols may be selected from: glycerol, pentaerythritol, 2,3-butanediol, mannitol, sorbitol, isoidide, isomannide, isosorbide, sorbitan and/or mixtures thereof. It is preferred that the polyol is from a biorenewable source.

Usefully alcohols may be present in the alkyd resin compositions in an amount of at least 10 wt-% and more preferably at least 20 wt-%, based on the total of weight of compounds a, b, c and d. Conveniently the alcohol may be present in the alkyd resin compositions in an amount of less than 40 wt-% more conveniently less than 35 wt-%, even more conveniently less than 30 wt-%, especially more conveniently less than 28 wt-%, most conveniently less than 25 wt-%, for example less than 22 wt-%, based on the total of weight of compounds a, b, c and d.

The alcohol may be present in the alkyd resin compositions in an amount of from 10 to 40 wt-%, preferably from 10 to 30 wt-%, more preferably from 15 to 25 wt-%, most preferably from 18 to 24 wt-%, for example 22 wt-% based on the total of weight of compounds a, b, c and d.

Fatty Acid and Vegetable Oil (Compound c)

The alkyd resin composition further comprises fatty acids and/or vegetable oil.

It will be appreciated that there is a difference between a fatty acid and/or fatty acid derivative and a vegetable oil. Typically what is referred to herein as "oil" denotes a mixture of glycerol esters of one or more fatty acids. Thus for example linseed oil denotes a natural product, whereas linseed oil fatty acid denotes a mixture of fatty acids prepared from linseed oil.

A fatty acid is a carboxylic acid with a long aliphatic tail, which is either saturated or unsaturated. Most naturally occurring fatty acids have a chain of an even number of carbon atoms, from 4 to 28 (preferably from 8 to 28). Fatty acids are usually derived from triglycerides or phospholipids. As used herein, the term fatty acid denotes a linear hydrocarbon carboxylic acid that comprises at least one ethylenically unsaturated double bond and preferred fatty acids comprise at least two ethylenically unsaturated double bonds or more preferably comprise at least one linoleically unsaturated moiety. However saturated fatty acids may still be present in the alkyd resin compositions for other reasons. Preferred fatty acids are linear $C_{12-60}$ hydrocarbon mono carboxylic acids comprising at least one linoleically unsaturated moiety. As used herein the term 'fatty acid' also encompasses precursors for fatty acids, i.e. any component that under the conditions for alkyd resin preparation will transform and/or react to form a fatty acid.

For alkyd resins, unsaturated fatty acids or oils having an iodine number of at least 100 cg/g, preferably from 120 to 200 cg/g, are preferred where isolated and conjugated double bonds may be present. They are obtained, for example, from vegetable sources, such as soy oil, sunflower oil, linseed oil, safflower oil, and cottenseed oil or originate from tall oil distillation. Fatty acids having conjugated double bonds are obtained by catalytic isomerisation of natural fatty acids, from tung oil, calendula oil and/or from dehydrated castor oil. Conjugated oil is preferably obtained by Isomerisation of non-conjugated fatty acids and/or by dehydration of castor oil. The iodine number is defined according to DIN 53 241-1 as the quotient of that mass ml of iodine which is added on to the olefinic double bonds, with decolourisation, of a sample to be analysed and the mass of this sample (mass of the solid in the sample in the case of solutions or dispersions); its conventional unit is "g/(100 g)" or "cg/g". In addition, saturated oils or saturated fatty acids having 10 to 22 carbon atoms can be used in part or completely, as long as oxidative drying of the resin obtained is not impaired.

The alkyd resin composition may comprise vegetable oil. The use of a vegetable oil is advantageous with regard to high availability and low cost. Examples of vegetable oils are unsaturated oils such as soybean oil, tall oil, tung oil, calendula oil, rosin, sunflower oil, dehydrated castor oil and linseed oil.

The alkyd resin composition may comprise mixtures of fatty acids and vegetable oils; such mixtures may comprise two types of vegetable oil or fatty acid (for example soybean oil together with tung oil), mixtures comprising a fatty acid and a vegetable oil of the same type (for example tung oil together with tung oil fatty acid), and mixtures comprising a fatty acid and a vegetable oil of different types (for example tung oil together with soybean fatty acid). Preferably, the unsaturated oils and derived fatty acids are more folded unsaturated oils and derivatives, i.e. oils or fatty acids having two, three or more double bonds. More preferred are tall oil, tung oil, calendula oil, rosin, sunflower oil, dehydrated castor oil, linseed oil, and corresponding fatty acids (for example tung oil fatty acid or soybean fatty acid). The most preferred are soybean fatty acid and/or tung oil, more preferred substantially tung oil. By substantially tung oil is here meant that only smaller amounts of other compounds are present.

In one embodiment the fatty acid and/or the vegetable oil has at least one eleostearic moiety. Herein by eleostearic moiety it is meant a moiety that consists of 3 conjugated double bonds. Examples of fatty acids or vegetable oils containing such moieties include among others eleostearic acid, tung oil or calendula oil. These have in their structure one or more eleostearic moeities. The advantage of using a fatty acid and/or vegetable oil containing an eleostrearic moiety is that the alkyd resin has a much better air-drying performance than using a non-eleostearic moiety containing fatty acid and/or vegetable oil. Tung oil is composed primarily of eleostearic acid which is an 18 carbon fatty acid having three conjugated double bonds (an eleostearic moiety).

Usefully fatty acids and/or vegetable oils may be present in the alkyd resin compositions in an amount of at least 30 wt-%, preferably of at least 35 wt-%, more preferably at least 40 wt-% and most preferably at least 50 wt-%, based on the total of weight of compounds a, b, c and d. Conveniently the fatty acids and/or vegetable oils may be present in the alkyd resin compositions in an amount of less than 70 wt-%, more conveniently less than 65 wt-%, even more conveniently less than 60 wt-%, especially more conveniently less than 58 wt-%, most conveniently less than 55 wt-%, based on the total of weight of compounds a, b, c and d.

The fatty acids or vegetable oils may be present in the alkyd resin compositions in an amount of from 30 to 70 wt-%, preferably from 40 to 60 wt-%, more preferably from 45 to 55 wt-%, for example 47 wt-% based on the total of weight of compounds a, b, c and d.

Mono or Polyfunctional Compound (Compound d)

The alkyd resin composition can optionally comprise an either biobased or non-biobased mono and/or polyfunctional compound capable of esterification, which compound is different from the compounds according to anyone of formulas Ia-e, the alcohol or the fatty acids or vegetable oils. Examples of mono and polyfunctional compounds capable of esterification are mono and polyfunctional compounds containing OH, COOH and/or NCO groups. Examples of such compounds containing OH and/or COOH groups are: Succinic acid lysine diimide or lysine disuccinimide (made from 1 mole of lysine and 2 moles of succinic acid or succinic anhydride), phenyl alanine succinimide (made from 1 mole of phenyl alanine and 1 mole of succinic acid or succinic anhydride), glycine succinimide (made from 1 mole of glycine and 1 mole of succinic acid or succinic anhydride), benzoic acid, succinic acid or succinic anhydride, adipic acid, sebacic acid, azelaic acid, terephthalic acid, phthalic acid, phthalic anhydride, trimellitic anhydride, citric acid, citric anhydride, citraconic acid, citraconic anhydride, isophthalic acid, itaconic acid, itaconic anhydride, tetrahydrophthalic acid, tetrahydrophthalic anhydride, hexahydrophthalic acid, hexahydrophthalic anhydride, monomethyl tetrahydrophthalic acid, monomethyl tetrahydrophthalic anhydride, monomethyl hexahydrophthalic acid, monomethyl hexahydrophthalic anhydride and/or any suitable mixtures thereof. Instead of the (di)carboxylic acids the corresponding alkyl esters may also be used. Examples of such compounds containing NCO groups are polyfunctional isocyanate compounds, preferably diisocyanates are used. Examples of polyfunctional isocyanate compounds are ethylene diisocyanate, 1,6-hexamethylene diisocyanate, isophorone diisocyanate, cyclohexane-1,4-diisocyanate, 4,4'-dicyclohexylmethane diisocyanate, p-xylylene diisocyanate, α,α'-tetramethylxylene diisocyanate, 1,4-phenylene diisocyanate, 2,4-toluene diisocyanate, 2,6-toluene diisocyanate, 4,4'-diphenylmethane diisocyanate, polymethylene polyphenyl polyisocyanates, 2,4'-diphenylmethane diisocyanate, 3(4)-isocyanatomethyl-1-methyl cyclohexyl isocyanate, 1,5-naphthylene diisocyanate, Desmodur HDTLV and mixtures thereof. Preferred polyisocyanates are isophorone diisocyanate, 4,4'-dicyclohexylmethane diisocyanate, toluenediisocyanate and 4,4'-diphenylmethane diisocyanate.

In an embodiment the mono and/or polyfunctional compound is present in such an amount such that the amounts of the compounds according to anyone of formulas Ia-e, the alcohol, the fatty acids, the vegetable oils and the mono and polyfunctional compound total 100 wt % and the amounts for each component in the alkyd resin composition also satisfy the preferred or more preferred amounts given for each component herein. The presence of the mono and polyfunctional compound is optional as in a yet further embodiment the mono and polyfunctional compound may also be absent (0% by weight) in the alkyd resin composition and for example the alkyd resin composition may then consist of the compounds according to anyone of formulas Ia-e, the alcohol, the fatty acids and/or vegetable oils.

Components or parts of components that do not fall within the definitions of the compounds according to anyone of formulas Ia-e, the alcohol, the fatty acids and/or vegetable oils and which components are capable of esterification are considered to form part of the optional mono or polyfunctional compound.

The amounts by weight for the compounds according to anyone of formulas Ia-e, the alcohol, the fatty acids and/or vegetable oils and the mono and/or polyfunctional compound given above are calculated based on the total being 100 wt %. If desired an esterification or trans-esterification catalyst can be used for the synthesis of the alkyd resin. Such catalysts are added on top of the total of the compounds according to anyone of formulas Ia-e, the alcohol, the fatty acids and/or vegetable oils and the mono and/or polyfunctional compound. Examples of such catalysts are tetrabutyl titanate, zinc acetate, Sn-compounds, like Sn-salts, monoalkyl Sn complexes etc.

There is an increasing demand to use bio renewable monomers in order to improve the sustainability of the resins used in for example coating applications. In view of concerns about depletion of fossil fuel resources or an increase in carbon dioxide in the air that poses a global scale environmental problem in recent years, methods for producing raw materials of these polymers from biomass resources have attracted a lot of attention. Since these resources are renewable and therefore have a carbon neutral biomass, such methods are expected to gain in particular importance in the future. It is therefore a preferred feature of the present invention and the aspects described herein that where possible the components used herein as far as possible are biorenewable.

Preferably at least 20 wt-%, more preferably at least 30 wt-%, and especially 40 wt-% of the components used to form the alkyd resin are derived from at least one biorenewable material. Biorenewable materials may be obtained fully or in part from biorenewable sources. Thus it is preferred to also measure the carbon-14 content to determine the biorenewability content of the components of the alkyd resin. The term bio-based is also used herein as a synonym for biorenewable (as defined herein).

The content of carbon-14 ($^{14}C$) is indicative of the age of a bio based material. It is known in the art that $^{14}C$, which has a half-life of about 5,700 years, is found in bio renewable materials but not in fossil fuels. Thus, "biorenewable materials" or "biomass" refer to organic materials in which the carbon comes from non-fossil biological sources. Examples of biorenewable materials include, but are not limited to, sugars, starches, corns, natural fibres, sugarcanes, beets, citrus fruits, woody plants, cellulosics, lignocellulosics, hemicelluloses, potatoes, plant oils, other polysaccharides such as pectin, chitin, levan, and pullulan, and a combination thereof. $^{14}C$ levels can be determined by measuring its decay process (disintegrations per minute per gram carbon or dpm/gC) through liquid scintillation counting. In one embodiment of the present invention, the alcohol component of the alkyd resin comprises at least about 1.5 dpm/gC (disintegrations per minute per gram carbon) of carbon-14, more preferably at least 2 dpm/gC, most preferably at least 2.5 dpm/gC, and especially at least 4 dpm/gC.

The invention also relates to an alkyd resin obtained by polycondensation of the compounds of the alkyd resin composition as defined above.

Therefore there is provided an alkyd resin (preferably having low VOC) obtained by reaction in a process (I) between the compounds according to anyone of formulas Ia-e, the alcohol, the fatty acids and/or vegetable oils and, optionally, the mono and/or polyfunctional compound to obtain an alkyd resin composition. VOC denotes volatile organic compounds which are organic compounds that have a boiling point from 50 to 250° C. under 1 atmosphere pressure. Low VOC denotes that the amount of VOC present is less than 100 g/l, if a liquid material and less than 100 g per kg if a solid material.

Another aspect of the present invention provides a process comprising a further optional blending step (II) performed after polycondensation process step (I) where step (II) comprises (II) adding a diluent to the alkyd resin obtained from step (I) to form an admixture therewith; wherein the diluent comprises an ethylenically unsaturated $C_{5-6}$ hydrocarbon dicarboxylic acid (preferably $C_5$ diacid), ester thereof and/or anhydride thereof, being reactive as a dienophile and/or enophile with the alcohol and/or the fatty acids and/or vegetable oils and/or (where present) the optional mono and/or polyfunctional compound;

wherein optional diluent is present in an amount of from 1 to 30 parts by weight with respect to 100 parts of the compounds according to anyone of formulas Ia-e, the alcohol, the fatty acids and/or vegetable oils and, optionally, the mono and/or polyfunctional compound from step (I).

The diluent may also be used as an additional reactant in process step (I) and/or as a diluent in the blending step (II). Examples of reactive diluents are dimethylitaconate, dibutylitaconate, α-methylene-γ-butyrolactone.

The invention also relates to a coating obtainable by applying a layer of the alkyd resin composition as defined above or a layer of the alkyd resin, obtained after polycondensation of the alkyd resin composition, on an object followed by curing of the layer.

The curing may be by any suitable means, such as thermally, by radiation, by oxidation (with oxygen from the atmosphere) and/or by use of a crosslinker.

Examples of coating compositions which can be used for obtaining a coating are aqueous coating compositions, solvent-borne coating compositions and powder coating compositions.

Optionally aqueous coating compositions may also comprise a co-solvent. A co-solvent, as is well known in the coating art, is an organic solvent employed in an aqueous composition to ameliorate the drying characteristics thereof, and in particular to lower its minimum film forming temperature. The co-solvent may be solvent incorporated or used during preparation of polymers or may have been added during formulation of the aqueous composition.

The coating composition is particularly useful as or for providing the principle component of coating formulations (i.e. composition intended for application to a substrate without further treatment or additions thereto) such as protective or decorative coating compositions (for example paint, lacquer or varnish) wherein an initially prepared composition optionally may be further diluted with water and/or organic solvents, and/or combined with further ingredients or may be in more concentrated form by optional evaporation of water and/or organic components of the liquid medium of an initially prepared composition.

The coating may be applied to a variety of substrates including wood, board, metals, stone, concrete, glass, cloth, leather, paper, plastics, foam and the like, by any conventional method including brushing, dipping, flow coating, spraying, and the like. The coating may also be used to coat the interior and/or exterior surfaces of three-dimensional articles. The carrier medium may be removed by natural drying or accelerated drying (by applying heat) to form a coating.

The alkyd resin coating composition may contain other conventional ingredients including pigments, dyes, emulsifiers, surfactants, plasticisers, thickeners, heat stabilisers, levelling agents, anti-cratering agents, fillers, sedimentation inhibitors, UV absorbers, antioxidants, dispersants, reactive diluents, waxes, neutralising agents, adhesion promoters, defoamers, co-solvents, wetting agents and the like introduced at any stage of the production process or subsequently. It is possible to include fire retardants (such as antimony oxide) to enhance the fire retardant properties.

The invention also relates to a resin composition for powder coating (further referred to as powder coating composition) comprising a'. 1-85 wt % of a compound according to anyone of formulas Ia, Ib, Ic, Id or Ie b'. 10-60 wt %, preferably 10-50 wt. % of a diol, c'. 0-80 wt. % of a diacid, d'. 0-40 wt % of a polyfunctional branching agent, having at least 3 functional groups selected from hydroxyl, carboxylic acid or anhydride wherein the wt % are calculated based on the total weight of compounds a', b', c' and d'.

The compounds according to formulas Ia, Ib, Ic, Id or Ie may be present in the powder coating compositions in an amount of at least 1 wt-% and preferably at least 5 wt-%, more preferably at least 10 wt %, based on the total weight of compounds a', b', c' and d'. Conveniently the compounds may be present in the powder coating compositions in an amount of less than 85 wt-% more conveniently less than 80 wt-%.

The compounds may be present in the powder coating compositions of the invention in an amount of from 1 to 85 wt-%, preferably from 5 to 80 wt-%, more preferably from 10 to 75 wt-%, based on the total weight of compounds a', b', c' and d'.

Diol (Compound b')

The powder coating composition comprises a diol. Suitable diols have a molecular weight of 62 to 500 and may optionally contain ether groups, ester groups, and/or carbonate groups. Suitable diols include, but are not limited to, ethylene glycol, 1,2-propanediol, 2-methyl-1,3-propanediol, 1,3-, 2,3- and 1,4-butanediol, 1,6-hexanediol, neopentylglycol, 1,3-propanediol, cyclohexanedimethanol, diethylene glycol, dipropylene glycol, neopentyl glycol bis (3-hydroxypropyl) ether, and mixtures of these diols. Other suitable diols include triethylene glycol, tetraethylene glycol, tripropylene glycol, tetrapropylene glycol, isosorbide, isoidide, isomannide, and mixtures of these diols. The reactive hydroxyl component can be simple monomeric units or oligomeric units or low molecular weight polymeric units. The preferred diols are aliphatic glycols such as 1,3-butylene glycol or 1,4-butylene glycol; ethylene glycol and propylene glycols; 2-methyl-1,3-propanediol, 1,6-hexanediol; isosorbide, isoidide, isomannide and neopentyl glycol.

The diol may be present in the powder coating compositions in an amount of at least 10 wt-% and more preferably at least 20 wt-%, based on the total weight of compounds a', b', c' and d'. Conveniently the diols may be present in the powder coating compositions in an amount of less than 50 wt-% more conveniently less than 40 wt-%, even more conveniently less than 30 wt-%, based on the total weight of compounds a', b', c' and d'. The diols may be present in the powder coating compositions in an amount of from 10 to 60 wt-%, preferably from 10 to 50 wt-%, more preferably from 10 to 40 wt-%, more preferably from 15 to 25 wt-%. based on the total weight of compounds a', b', c' and d'.

Diacid (Compound c')

The powder coating composition comprises a diacid (different than compound a). Suitable diacids include, but are not limited to, sebacic acid, isophthalic acid, terephthalic acid, adipic acid, cyclohexanedicarboxylic acid, succinic acid, dimer fatty acid, fumaric acid, maleic anhydride, itaconic acid and mixtures thereof. The diacids may be present in the powder coating compositions in an amount of at most 80 wt-%, preferably in an amount of at most 30 wt-%, more preferably at most 25 wt-%, more preferably at most 20 wt-%, more preferably at most 15 wt-%, and even more preferably at most 10 wt-%, based on the total weight of compounds a', b', c' and d'.

Branching Agent (Compound d')

The powder coating composition can comprise a polyfunctional branching agent, having at least 3 functional groups selected from hydroxyl, carboxylic acid or anhydride. The branching agent can, for example, be a triol or higher alcohol. Suitable branching agents include, but are not limited to trimethylolethane, trimethylolpropane, trimellitic anhydride, glycerol, pentaerythritol, dipentaerythritol, sorbitol and citric acid. If present, the branching agent may be present in the powder coating compositions in an amount of 1 wt-% and more preferably at least 2 wt-%, based on the total weight of compounds a', b', c' and d'. Conveniently the branching agent may be present in the powder coating compositions in an amount of less than 40 wt-% more conveniently less than 30 wt-%, even more conveniently less than 25 wt-%, based on the total weight of compounds a', b', c' and d'.

The branching agent may be present in the powder coating compositions of the invention in an amount of from 1 to 40 wt-%, preferably from 2 to 30 wt-%, more preferably from 5 to 25 wt-%, based on the total weight of compounds a', b', c' and d'.

The term "powder" as used herein indicates a composition that comprises a collection of loose solid particles wherein the individual particles have a maximum particle size of at most 200 μm at 23° C. and at atmospheric pressure, for example a particle size of at most 150 μm, for example of at most 100 μm at 23° C. and at atmospheric pressure. A powder that is in a form suitable for application to a substrate as a coating (optionally formulated with other ingredients) is also referred to herein as a 'powder coating composition', although such compositions depending on the context, can also just be referred to herein as 'powders'. The term 'powder coating' as used herein is the partially or fully cured (crosslinked) form of the powder coating composition after it has been applied to a substrate. In other words the powder coating is derived upon partial or full cure of a powder coating composition (or powder).

Powders of the invention may have some or all of the following general characteristics. Powders are dry, finely divided, free flowing, solid materials at room temperature and at atmospheric pressure. Powders are benign to the user and the environment since they are virtually free of volatile organic solvents and emit little, if any, volatile materials when cured. Powders are also clean and convenient to use since they are applied to the substrate in dry solid form. Powders are easily collected if spilt and do not require special cleaning or containment supplies, so improving working hygiene. Powders are essentially 100% recyclable since sprayed powders can be fully reclaimed and recombined with fresh powder feed. Powder coating compositions can be prepared ready to use as no thinning or dilution is required before coating.

Powders comprise finely divided particles of the resins. Optionally if the powder is a thermosetting powder, the composition may also comprise a crosslinker. Powders also usually contain pigments, fillers, and other additives like flow agents, degassing agents, curing catalysts and the like.

After application to the substrate, for example by electrostatic spraying or dipping, the individual powder particles are melted in an oven and coalesce to form the powder coating as a continuous film. Powder coatings have decorative and protective properties associated with conventional organic coatings. Powders are applied by fusion-coating processes as during the coating process the powder particles are fused or melted. Although this is usually carried out in a convection oven, infrared, resistance, and induction heating methods have also been used. Therefore, with minor exceptions, powder coatings are usually applied in factories using fixed installations and are less commonly used in repair or maintenance applications. Powders are typically applied to a substrate using an electrostatic spray process; the powder being dispersed in an air stream and passed through a corona discharge field where the particles acquire an electrostatic charge. The charged particles are attracted to and deposited on the grounded object to be coated. The object (usually sprayed at room temperature), is then placed in an oven where the powder melts to form a powder coating. A hybrid application process has also been developed using a combination of high voltage electrostatic charging and fluidized-bed techniques (such as electrostatic fluidized bed). Powders have also been applied by triboelectric methods. Powders are widely used to coat many familiar items such as white goods like lawn and garden equipment, patio and other metal furniture, electrical cabinets, lighting, shelving, store fixtures and many automotive components, wood products, plastic products and/or any substrates where low temperature curing is desirable. Powder coatings are widely used with thousands of installations in the factories of original equipment manufacturers (OEMS) and custom coating job shops.

Powder coating compositions can be thermosetting or thermoplastic. Preferably the powders of the present invention are thermosetting powder coating compositions. The preparation of thermosetting powder coating compositions is described by Misev in "Powder Coatings, Chemistry and Technology" (pp. 224-300; 1991, John Wiley).

Resins that are particularly suitable for use in a powder coating composition are those resins that are solid at 23° C. and at atmospheric pressure (e.g. under Standard Conditions).

In preferred powder coating compositions the glass transition temperature (Tg) of the resin is at least 40, more preferably at least 42, even more preferably at least 45, most preferably at least 48, for example at least 50° C. The glass transition temperature (Tg) of the resin is preferably at most 100, more preferably at most 90 even more preferably at most 80, most preferably at most 75, for example at most 70° C.

The glass transition temperature (Tg) of the uncured (optionally thermosetting) powder coating composition of the invention is preferably at least 20° C., more preferably at least 25° C., even more preferably at least 35° C., most preferably at least 45° C. The glass transition temperature (Tg) of the uncured thermosetting powder coating composition is preferably at most 100° C., more preferably at most 90° C., even more preferably at most 80° C., most preferably at the most 70° C.

The invention is also directed to a polyester comprising the compounds of formulas Ia, Ib, Ic, Id or Ie.

The invention is further directed to the use of the compounds of formulas Ia, Ib, Ic, Id or Ie to make a polymer or resin composition.

The invention is also directed to an object containing coating layers obtainable by the application of the alkyd resin composition described above followed by curing. The invention is also directed to an object containing coating layers obtainable by the application of the powder coating composition as described above.

The present invention further relates to an alkyd emulsion comprising an alkyd resin as described above, which emulsion is water borne, and where optionally at least one surfactant (preferably a mixture of nonionic and ionic surfactants) is added after the reaction of Components a, b, c and d and/or where optionally at least one surfactant (preferably a mixture of nonionic and ionic surfactants) is added during the reaction of components a to d. The present invention further also relates to an alkyd resin as described above which is solvent borne or a solid.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention is now elucidated by way of the following examples, without however being limited thereto.

EXAMPLES

Unless otherwise indicated all the tests herein are carried out under standard conditions as also defined herein.

Acid Number

The acid number (or AN) is given as the mass of potassium hydroxide (KOH) in milligrams that is required to neutralize one gram of the tested substance and is used as a measure of the concentration of carboxylic acid groups present. AN is determined conventionally by titration and/or using ASTM D974.

Gloss Measurement Method:

Gloss measurements were carried out on a BYK Gardner micro TRI gloss 20 60 85 glossmeter in accordance with ASTM D523 89.

König Hardness

König hardness was determined following DIN 53157 NEN 5319 using an Erichsen hardness equipment. The values are given in seconds (s). Preferably the unpigmented composition of the invention has a König hardness of at least 30 seconds after 4 weeks.

Molecular Weight Determination (Weight Average Mw (g/mol)):

Unless the context dictates otherwise, the molecular weights referred to in this application are weight average molecular weight (also denoted herein as Mw) as determined on an Alliance Waters 2695 GPC with two consecutive PL-gel columns, type Mixed-C, I/d=300/7.5 mm (Polymer Laboratories), size of column particles 10 µm, using stabilised tetrahydrofuran (THF) modified with 0.8% acetic acid as the eluent at 1 mL/min at 40° C. and using an Alliance Waters 2414 refractive index detector at 40° C. A set of polystyrene standards with a molecular weight range of from 500 to $7 \times 10^6$ g/mol was used to calibrate the GPC equipment.

Molecular Weight Determination (Number Average Mn (g/mol)):

Unless the context dictates otherwise where a number average molecular weight (also denoted herein as Mn) is mentioned this is measured using the same apparatus in the manner described above.

Standard Conditions

As used herein, unless the context indicates otherwise, standard conditions (e.g. for drying a film) means a relative humidity of 50%±5%, ambient temperature (23° C.±2°) and an air flow of less than or equal to 0.1 m/s.

Drying Properties (Cotton Wool Dust Free Time (DFT) and Tack Free Time (TFT) Tests).

A cotton wool adhesion test measures the rate of surface drying of a coating film. The cotton wool adhesion test was conducted on a coating film applied with a 100 µm slit applicator on a glass plate. After applying the coating composition, a swatch of cotton wool (a loose ball of approximately 0.2 g and a diameter of approximately 3 cm) was dropped from a height of 5 cm on the paint film. After 10 seconds the glass panel was turned over 180° and it was observed if the cotton wool dropped off without leaving cotton fibres on the surface. When the cotton wool did not stick to the surface, the time was recorded as the dust free time. For the tack free time the same procedure was used, but now a weight of 1 kg was placed on the cotton wool. The tack free time was always determined after dust-free properties were reached.

Water Resistance:

A 100 µm wet film was cast on a Leneta chart and dried for 24 hours under standard conditions. Then three drops of water were placed on the film and one drop of water was removed after 30 minutes, a further one after one hour and the final one after 3 hours. The water resistance was assessed immediately after removal of the water and after 24 hours. The rating for water resistance is from 0=very poor, dissolved, 3=acceptable, 5=excellent, no damage of the coating.

Water resistance can also be measured quantitatively using the following test. The composition to be tested is applied to a film as described above in the wet adhesion test. The coated test specimens were soaked in tap water at 40 degrees C. for seven days at room temperature (20 degree C.). The weight gain was recorded at end of this period (and at suitable intervals throughout) to calculate the relative water uptake of the specimens.

Yellowing:

Colour change due to yellowing is measured according to CieLab. A coating film is applied with a 100 µm slit applicator on a glass plate and dried for one week at room temperature. Then initial colour according to CieLab (L-value, a-value, b-value) is measured and b-value recorded. Next the film is stored in an oven at 50° C. for one week. Again colour is measured and change in b-value is recorded as Δb. The higher Δb, the stronger the yellowing is.

Glass Transition Temperature

Glass transition temperatures Tg of alkyd resins have been determined by DMTA. Resin solutions in xylene were applied on a glass plate using a film applicator. After a period of 24±3 hours of drying, part of the film was removed from its substrate using a razor blade. Subsequently the film was reshaped into a cylindrical sample containing a 16-fold stacked film with a diameter of 8 mm and a height of 480±50 µm.

These samples were inserted into the 8 mm diameter plate/plate system of a Physica MCR301 rheometer, at a temperature of 40° C. After clamping of the sample between the plates, the temperature is raised up to 90° C. and a Normal Force is applied in order to get optimal filling and adhesion. Subsequently the actual DMTA measurement is started by lowering the temperature down to −25° C. at a cooling rate of −4° C./min. While cooling the sample is subjected to an oscillatory shear deformation with amplitude (γo) of 0.001 strain unit and a frequency of 1 Hz. From the amplitude of the required oscillatory shear stress (τo) the complex (shear) modulus, G* is calculated as a function of temperature:

$$G^* = \tau o / \gamma o$$

G*(T) represents the stiffness of the resin film as a function of temperature.

Here the Tg has been defined as the temperature corresponding with a complex modulus of 107 Pa.

Experiment Imide 1: Phenylalanine with Citraconic Anhydride

As an example citraconic acid phenylalanine imide was prepared in a 250 cm$^3$ round bottomed flask, fitted with mechanical stirrer, nitrogen inlet, thermocouple and Dean-Stark trap. Citraconic anhydride (51.04 g, 0.4557 mol) and phenylalanine (78.96 g, 0.4785 mol) were added in a [1:1.05] mole ratio and reacted 5 hours at 145° C. using xylene as an azeotropic agent for water removal. The set up was then changed to a distillation bridge and vacuum distillation was performed to remove the xylene from the reaction mixture (Similar syntheses involved the use of a distillation bridge only with the same results produced).

NMR and IR analysis confirmed that imide has been formed in high purity.

Experiment Imide 2: Glycine with Citraconic Anhydride

Citraconic acid glycine imide was prepared in a 250 cm$^3$ round bottomed flask, fitted with mechanical stirrer, nitrogen inlet, thermocouple and Dean-Stark trap. Citraconic anhydride (76.3 g, 0.681 mol) was added to glycine (53.7 g, 0.715 mol) in a [1:1.05] mole ratio and reacted 5 hours at 145° C. using xylene as an azeotropic agent for water removal. The set up was then changed to a distillation bridge and vacuum distillation was performed to remove the xylene from the reaction mixture.

NMR and IR analysis confirmed that imide has been formed in high purity.

Experiment Imide 3: Lysine with Succinic Acid

Succinic acid lysine diimide was prepared as follows: A 50% solution of 765.3 grams succinic acid in xylene was heated to 125° C. in a 3 liter glass reactor, fitted with mechanical stirrer, nitrogen inlet, thermocouple and Dean-Stark trap. 782.5 grams of a 53% solution of lysine in water (commercially available from Ajinomoto Eurolysine SAS as LLB-50) was dosed during 2 hours while removing water azeotropically. Water removal is continued until no reaction water is formed anymore and xylene is distilled off at maximum 160° C. The brown viscous liquid material was poured out and solidified into a brittle and clear solid.

Example 1: Glycine Based Citraconimide with Sorbic Acid

In a 700 cm$^3$ pressure reactor sorbic acid (73.89 g, 0.660 mol) was added to an imide of citraconic anhydride and glycine (111.4 g, 0.660 mol) in a ratio of 1:1. Water (150 g) was then added and the reactor vessel sealed and the reaction proceeded at 150° C. for 5 hours. The contents of the reactor vessel were then poured into a round bottomed flask and left on the rotary evaporator to remove the solvent (water). Subsequent syntheses on larger scale (5 dm$^3$ pressure reactor) have involved the same ratio of citraconimide:sorbic:water and have involved the removal of water to be performed in a distillation set up instead of rotary evaporator.

NMR analysis showed presence of conjugated and non-conjugated tautomeric adducts as well as small amounts of sorbic acid and dimerized sorbic acid. Residual imide was not found.

Example 2: Phenylalanine Based Citraconimide with Sorbic Acid

In a process according to example 1 the imide of phenylalanine and citraconimide (85.7 g, 0.33 mol) was added to sorbic acid (39.2 g, 0.35 mol) in a ratio of 1.06:1, using water as a solvent (150 g).

Example 3: Alkyd Containing Glycine Citraconimide Sorbic Adduct

An alkyd resin based on adduct from example 1 was prepared in a 250 cm$^3$ round bottomed flask, fitted with mechanical stirrer, nitrogen inlet, thermocouple and Dean-Stark trap. 26.4 grams pentaerythritol, 45.7 grams soybean oil fatty acids, 40.0 grams glycine citraconimide sorbic acid adduct, 22.5 grams lysine succinimide prepared according experiment imide 3, 3.6 grams sebacic acid and 1.8 grams succinic acid were reacted at max 200° C. using xylene azeotropic agent. After reaction for 8 hours an acid value of 18 was obtained and the mixture was cooled down, diluted with xylene and poured out.

The resin showed Tg=32° C. and Mn/Mw=2800/20800.

Example 4: Alkyd Containing Phenylalanine Citraconimide Sorbic Adduct

An alkyd resin based on adduct from example 2 was prepared in a 250 cm$^3$ round bottomed flask, fitted with mechanical stirrer, nitrogen inlet, thermocouple and Dean-Stark trap. 24 grams pentaerythritol, 41.5 grams soybean oil fatty acids, 48.2 grams phenylalanine citraconimide sorbic acid adduct, 20.5 grams lysine succinimide prepared according experiment imide 3, 3.3 grams sebacic acid and 1.8 grams succinic acid were reacted at max 200° C. using xylene azeotropic agent. After reaction for 8 hours an acid value of 15 was obtained and the mixture was cooled down, diluted with xylene and poured out.

The resin showed Tg=32° C. and Mn/Mw=2300/10200.

Comparative Example Comp A

A comparative alkyd resin A was prepared by reacting 168.2 grams of phthalic anhydride (PA), 155.4 grams of pentaerythritol, 96.2 grams of benzoic acid and 217 grams of soyabean fatty acids at max 230° C. Esterification was conducted by azeotropic water removal until acid value below 15 mgKOH/g. The resin was cooled down, diluted in xylene and poured out. The resin showed Tg=16° C. and Mn/Mw=4200/38200.

Examples 5 and 6: Paints

Paints were produced by mixing in a Cowless dissolver resin solution (44 grams solid resin), 28 grams of Tioxide TR 92 (pigment) and 0.30 grams of Nuosperse FA 601 (dispersant) and milling them into a mill paste. To this paste were added under stirring 0.31 grams Borchi-Oxy-Coat (iron drier), 0.70 grams Calcium naphthenate (calcium drier), 1.83 grams Octasoligen Zirconium 12 (zirconium drier), 0.3 grams Borchinox M2 (antiskinning agent) and xylene to give application viscosity.

These paints showed the following properties (table).

| Paint | Paint A1 | Ex 5 | Ex 6 |
|---|---|---|---|
| Example resin used in paint | Comp A | Ex 3 | Ex 4 |
| Based on diacid monomer | PA | Ex 1 | Ex 2 |
| Cotton wool drying, 100 µm wet | | | |
| dust free time (hr:min) | 0:32 | 0:10 | 0:20 |
| tack free time (hr:min) | 3:12 | 0:20 | 0:27 |
| König Hardness in sec, 100 µm wet | | | |
| 1 day | 32 | 40 | 61 |
| 7 days | 59 | 84 | 102 |
| 14 days | 69 | 90 | 104 |
| 28 days | 90 | 102 | 114 |
| Yellowing in the dark, 100 µm wet | | | |
| b* Initial | 2.32 | 2.72 | 2.97 |
| db* after 14 days 50° C. | 0.74 | 1.35 | 1.23 |
| db* after 21 days 50° C. | 1.87 | 2.35 | 2.20 |
| Water resistance (rating 1-5, 5 best) | | | |
| Average 0.5/1.5/3 Hrs | 4.5 | 4.5 | 4.5 |
| Average recovery 24 Hrs | 5.0 | 4.5 | 4.5 |

The results show that the paints (Examples 5 and 6) formulated with resins containing adducts of the invention show better hardness and drying results in comparison with prior art Paint A1. Moreover, examples 5 and 6 have a significantly higher biobased content compared to comparative experiment A1.

Example 7: Paint Based on Uralkyd Containing Phenylalanine Citraconimide Sorbic Adduct of Example 2

First the following polyols were prepared:
Polyol I—Fatty Acid Modified Polyester Polyol Neopentyl glycol (8.35 g), trimethylolpropane (11.53 g) and 5-lithium(sulfo)isophthalic acid (11.00 g), pentaerythritol (13.59 g), phenylalanine citraconimide sorbic adduct (32.72 g) and decanedioic acid (5.16 g) were heated in a reactor to 220° C. with the removal of the reaction product (water) till an acid value of <25 mg KOH/g. After completion soybean oil fatty acid (80.14 g) was added and heated to 220° C. removal of the reaction product (water) until an acid number of <5 mgKOH/g was reached.

After cooling the resultant fatty acid modified polyester polyol (Polyol I) was dissolved in acetone to a solids content of 80%. Polyol I had a theoretical hydroxyl value of 60 mgKOH/g.

Polyol II—Fatty Acid Modified Polyester Polyol

Soybean fatty acid (224.7 g), di-succinic lysine imide (53.8 g), pentaerythritol (112.7 g) and Phenylalenine citraconimide sorbic adduct (217.7 g) were heated in a reactor at temperatures up to 200° C. in the presence of xylene (40 g) as an entraining agent, with the azeotropic removal of the reaction product (water) until an acid number of <12 mgKOH/g was reached. After completion of the reaction the azeotropic xylene was removed by vacuum distillation at 200° C. at 0.3 bar. After cooling the resultant fatty acid modified polyester polyol (Polyol II) was dissolved in acetone to a solids content of 74%. Polyol II had a theoretical hydroxyl value of 70 mgKOH/g.

Water-Based Emulsion of Uralkyd Containing Phenylalanine Citraconimide Sorbic Adduct of Example 2

Fatty acid modified polyester polyol (120.0 g) (Polyol I as prepared above in acetone), neopentylglycol (19.2 g), Desmodur I, (supplied by Bayer, cycloaliphatic diisocyanate based on IPDI, 3-isocyanatomethyl-3,5,5-trimethylcyclohexyl isocyanate, NCO content 37.5% minimum, 56.5 g), Coscat 83 (Supplied by Vertellus, Bismuth type catalyst (1.08 g)), Ymer N120 (14.4 g) and acetone (155.2 g) were heated in a reactor at 60° C. until the NCO content was 0.27%. The reaction mixture was cooled to 50° C. and fatty acid modified polyester polyol (146.57 g) (Polyol II as prepared above in acetone) was added. The reaction was continued at 60° C. until the NCO content was <0.05%. The resultant uralkyd resin was cooled to 45° C. and dispersed in demineralised water (408.37 g) and the acetone was removed by distillation. The resultant dispersion was adjusted with demineralised water to a solids content of 40%.

Paint Based on Water-Based Uralkyd Resin as Described Above

A paint was produced by mixing in a Cowless dissolver 5.40 grams of demineralized water, 0.32 grams Byk 028, 1.15 grams Nuosperse FX 610, 1.15 grams Rheolate 212 and 23 grams of Kronos 2190 (pigment) and milling them into a fine dispersion. To this dispersion were added under stirring the water-based emulsion of uralkyd containing phenylalanine citraconimide sorbic adduct prepared as described above (26 grams solid resin), 1.70 grams BorchiOXY-Coat 1101 (11%) and 2.00 grams Rheolate 212.

The above coating formulation was applied to a substrate to form a top coat thereon and various parameters of the coating were measured (as described in the test methods herein below). The results are given in the following table

| Paint of Ex 7 | |
|---|---|
| Tack free time (h:mm) | 0.22 |
| Water resistance | 5.0 |
| 20° Gloss after 4 weeks | 74 |
| König hardness after 4 weeks | 88 |
| Yellowing db after 3 weeks | 2.60 |
| Blocking resistance | 5 |

The above tested imide based coating showed surprisingly a high hardness, fast drying, good water resistance and blocking resistance.

Drying

Paints are applied by using a film applicator with a gap size of 100 micron on glass. The coated test panels are dried at room temperature.

To determine the tack free time, a piece of cotton-wool is pressed on the paint surface with a weight of 1 kg for 10 seconds. After removal of the weight, the glass panel is turned. When the cotton wool falls without any pieces sticking to the surface, the coating has reached it tack free time.

Water Resistance

Paints are applied by a film applicator on a glass panel. The coated test panels are dried at room temperature for 24 hours. On these films three drops of demineralized water with a diameter of approximately 10 mm were applied with pipette, making sure the distance to the edge of the coating and to the other drops is at least 10 mm. After the desired period (standard 30 min, 1 hour and 3 hours) the drops of water are carefully removed with a paper tissue. Note the visible damage of the coating and check the recovery of the film on the spots 24 hours after removal of the water spot. Give a rating from 5 (=excellent) to 0 (=poor).

Blocking Resistance

Paints are applied on Leneta foil (Black Scrub Test Panel) using a wire rod with a wet film thickness of 100 micron. The coated test panels are dried at room temperature for 24 hours. Out of the films, pieces of 2×2 cm were cut and pressed together, paint film facing paint film, for 2 hours at 50° C. A pressure of 250 g/cm$^2$ was used. The pieces were separated manually and the degree of damaging to the coating (0=very poor, 5=excellent) and the percentage of the surface that actually delaminated from the Leneta was assessed.

König Hardness

Paints are applied by using a film applicator with a gap size of 100 micron on a glass panel. The coated test panels are dried at room temperature and hardness in seconds is determined using König pendulum tester after 1, 7 and 28 days.

Gloss

Paints are applied by using a film applicator with a gap size of 100 micron on white PVC. The coated test panels are dried at room temperature and gloss at 20°, 60° and 85° are determined after 1, 7 and 28 days.

Yellowing

Paints are applied using a film applicator with a gap size of 100 micron on Leneta foil (Black Scrub Test Panel). The coated test panels are dried at room temperature. The colour is measured according to CieLab (L-value, a-value, b-value) after 7 days after which the panel is placed in a stove at 50° C. Again the colour is measured after 1, 2 and 3 weeks. Yellowing is determined as delta b as change in b value after 3 weeks compared to the initial measurement.

Powder Coating

Measurements Powder Resins

Glass Transition Temperature

The glass transition temperature of the resin (Tg in ° C.) was measured via Differential Scanning Calorimetry (DSC) on a TA instruments DSC Q20 apparatus, in $N_2$ atmosphere calibrated with indium. The processing of the signal (DSC thermogram, Heat Flow vs. Temperature) was carried out using Universal Analysis 2000 software version 4.5a provided by TA instruments, as described herein after:

A sample of 8±5 mg was weight and placed in the DSC cell. The sample was heated to 150° C. and the temperature was kept at 150° C. for 10 minutes after which the sample was cooled to 0° C. as fast as possible followed by an equilibration. The sample was heated up to 100° C. at a heating rate of 5° C./minute and the resulting thermogram was analyzed in which the Tg is reported as the inflection point over which the glass transition took place (defined in § 3.2.1.3 in ASTM E 1356-08).

Acid and Hydroxyl Value

The acid (AV, mg KOH/g of polyester) and hydroxyl (OH, mg KOH/g of polyester) values of the polyester resins were determined titrimetrically according to ISO 2114-2000 and ISO 4629-1978.

Viscosity Measurements

Viscosity measurements were carried out at 160° C. using the Brookfield CAP 2000+ Viscometer. This is a cone and plate rheometer which was used with a spindle CAP-S-05 at 21 rpm (shear rate 70 s$^{-1}$) and the viscosity is given as Pa·s.

Measurements and Assessments of Properties of Powder Coatings

The properties of the powder coatings were assessed using untreated aluminum (AlMg3) panels with a thickness of 1 mm. These panels were cured for 15 minutes in a gradient oven, BYK-Gardner GmbH Gradient Oven, and the oven and panel temperature ranged from 150° C. to 250° C. in a linear temperature gradient over the complete length of the oven and that of the panel).

Coating thickness was measured by a PosiTector 6000 coating thickness gage from DeFelsko Corporation and measurements were done on coating thicknesses of 50±15 µm.

Gloss and haze of the powder coatings of the thermosetting powder coating compositions were measured with a BYK-Gardner GmbH Haze-Gloss meter. The gloss is reported at angles of 20° and 60° in gloss units together with the measured haze.

For adhesion the so-called Gitterschnitt test was performed as described in DIN EN ISO 2409 and the adhesion is assessed with values from Gt0 (excellent adhesion) to Gt5 (no adhesion).

The degree of cure was assessed by acetone double rubs on the panel and the temperature where the coating could withstand 100 double rubs is regarded as full cure. This test is executed with a modification from ASTM D5402-06 (2011) with a cloth wrapped around a hammerhead of 1 kg on the round side. The cloth was dipped in acetone and with the handle the cloth was manually rubbed over the coating and the amount of double rubs needed to remove the coating from the substrate is given (optical verification of the substrate). A value of 100 indicates that the coating was not removed from the substrate with 100 double rubs.

Example 8

A polyester resin for powder paints was made by mixing 202.3 grams of the glycine based citraconimide with sorbic acid from example 1 with 56.3 grams of 1,3-propanediol and 17.5 grams of sebacic acid in a reactor vessel fitted with a thermometer, a stirrer and a distillation device. 0.1 Grams of a mono-alkyltin catalyst was added and under a nitrogen flow the mixture was heated while stirring. The temperature was gradually increased to 240° C. while distilling of water until no distillate is coming of anymore. Subsequently reduced pressure was used until the polyester reached the desired AV. The end values were AV=33 mg KOH/g, OH=5 mg KOH/g, viscosity=17.4 Pa·s and Tg=56° C. During the synthesis the process was measured regularly and if needed corrections were done by using either the acid from example 1 or 1,3-propanediol to ensure end-values of AV appr. 35 and OH<=5.

The Tg of this resin is sufficiently high for use in powder coatings which shows that the glycine based citraconimide sorbic modified diacid is an alternative for phthalic acids to obtain solid resins at room temperature.

Example 9

A second resin was made similarly as in example 8 with a filling of 204 grams acid from example 1, 48.3 grams 1,3-propanediol, 4.7 grams glycerol, 17.4 grams sebacic acid and 0.1 grams of tin catalyst. The corrections during synthesis were based upon AV=52 and OH<=5 and the end values reached were AV=50 mg KOH/g, OH=4 mg KOH/g, viscosity=35.0 Pa·s and Tg=62° C.

Examples 10 and 11

Powder paints were made from the resins obtained in examples 8 and 9. The thermosetting powder coating compositions were prepared by mixing the components presented in the below table in a blender and subsequently extruding in a PRISM TSE16 PC twin screw at 125° C. in which the screw speed was adapted to have a high torque to ensure good mixing. The extrudate was allowed to cool to room temperature and broken into chips. The chips were milled in a Retsch ZM100 with a 0.5 mm ring sieve at 18000 rpm and then sieved. The sieve fraction with particle size below 90 μm was collected.

The chemicals used to prepare the thermosetting powder coatings are Primid® XL-552 ($T_{melt}$=120-124° C., hydroxyl value 620-700 mg KOH/g of the Primid® XL-552) which is a crosslinker from EMS Chemie, Kronos® 2310 is titanium dioxide from Kronos Titan GmbH and Resiflow® PV 5 is a flow control agent from Worlée-Chemie GmbH. Benzoin is used as degassing agent.

| Paint | Example 10 | Example 11 |
|---|---|---|
| Resin example 8 (g) | 95.00 | |
| Resin example 9 (g) | | 93.00 |
| Primid ® XL-552 (g) | 5.00 | 7.00 |
| Kronos ® 2310 (g) | 50.00 | 50.00 |
| Resiflow ® PV 5 (g) | 1.50 | 1.50 |
| Benzoin (g) | 0.75 | 0.75 |

The powder coating compositions prepared as above were electrostatically sprayed (corona, 60 kV) onto the gradient panel and cured in the gradient oven from 150 to 250° C. for 15 minutes. Smooth films with a good appearance were formed throughout the temperature range cured.

Both coatings are high gloss and show good adhesion on the aluminum panel if cured properly. Full cure is reached above 200° C. looking at the acetone double rubs.

The invention claimed is:

1. An imide compound according to any one of formulas Ia, Ib, Ic, Id or Ie:

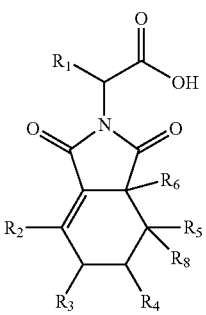

Ia

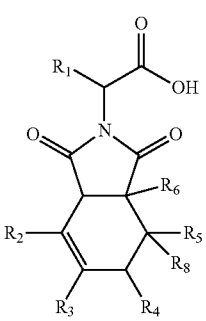

Ib

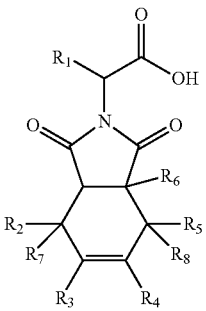

Ic

| | Paint | | | | | | | | |
|---|---|---|---|---|---|---|---|---|---|
| | Example 10 | | | | | Example 11 | | | |
| | Temperature on gradient panel (° C.) | | | | | | | | |
| | 160 | 170 | 200 | 230 | 240 | 160 | 170 | 200 | 230 | 240 |
| Thickness (μm) | 42 | x | 35 | 46 | x | 54 | x | 50 | 60 | x |
| Gloss 20°/60°/haze | x | 77/87/29 | 72/86/80 | x | 60/83/150 | x | 65/85/117 | 55/82/219 | x | 36/74/249 |
| Gitterschnitt (Gt) | 0 | x | 0 | x | x | 3 | x | 0 | x | x |
| Acetone double rubs | 67 | x | 95 | 100 | x | 61 | x | 87 | 100 | x | x: not measured

-continued

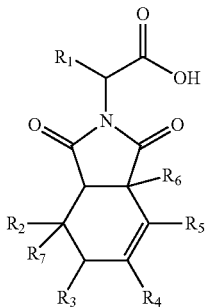

Id

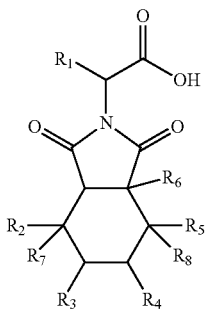

Ie wherein R₁ is H, methyl, hydroxymethyl, 1-hydroxyethyl, isopropyl, sec-butyl, 2-methyl-propyl, 2(methylthio) ethyl, benzyl, tolyl, parahydroxytolyl, or an organic fragment of an amino acid selected from the group consisting of arginine, histidine, lysine, aspartic acid, glutamic acid, serine, threonine, asparagine, glutamine, cysteine, selenocysteine, glycine, proline, alanine, valine, isoleucine, methionine, phenylalanine, tyrosine and tryptophan;

both $R_2$ and $R_5$ are a COOH group or one of $R_2$ and $R_5$ is a COOH group while another of $R_2$ and $R_5$ is H, methyl or an ethyl group;

$R_3$ and $R_4$ are independently H or a C1-C20 hydrocarbon group;

$R_6$ is H or a methyl group; and $R_7$ and $R_8$ are independently H, methyl or ethyl.

2. The compound according to claim 1, wherein $R_6$ is a methyl group.

3. The compound according to claim 1, wherein $R_1$ is selected from H, methyl, hydroxymethyl, 1-hydroxyethyl, isopropyl, sec-butyl, 2-methyl-propyl, 2(methylthio)ethyl, benzyl, tolyl and parahydroxytolyl.

4. The compound according to claim 1, wherein $R_1$ is selected from H and benzyl.

5. The compound according to claim 1, wherein one of $R_2$ and $R_5$ is a COOH group, while another of $R_2$ and $R_5$ is H, methyl or an ethyl group.

6. The compound according to claim 1, wherein one of $R_2$ and $R_5$ is a COOH group, while another of $R_2$ and $R_5$ is methyl.

7. The compound according to claim 1, wherein $R_3$ and/or $R_4$ is H.

8. A polyester prepared from a compound according to claim 1.

9. A polyester comprising a compound according to claim 1.

10. A resin composition comprising at least one compound according to claim 1.

11. An alkyd resin composition comprising:
    (a) 1-60 wt % of a compound according to claim 1;
    (b) 10-40 wt % of an alcohol having a number average hydroxyl functionality ≥2.0; and
    (c) 30-70 wt % of fatty acids and/or vegetable oils,
    wherein
    the wt % is determined relative to total of weight of compounds (a), (b), and (c).

12. An alkyd resin obtained by polycondensation of an alkyd resin composition according to claim 11.

13. A coating obtained by applying a layer of the alkyd resin according to claim 12 on an object followed by curing of the layer.

14. A process of making a polymer or a resin composition using a compound according to claim 1.

15. An object containing coating layers obtained by application of the alkyd resin according to claim 12 followed by curing.

16. An alkyd emulsion comprising an alkyd resin according to claim 12, wherein the alkyd emulsion is water borne.

17. A resin for powder coatings, wherein said resin composition comprises
    (a') 1-85 wt % of a compound according to anyone of formulas Ia, Ib, Ic, Id or Ie, as claimed in claim 1,
    (b') 10-60 wt % of a diol, and
    (c') 0-80 wt % of a diacid, wherein
    the wt % are calculated relative to the total weight of compounds (a'), (b'), and (c').

18. A resin powder coatings prepared from a resin composition according to claim 17.

19. A thermosetting powder comprising a resin according to claim 18.

20. A powder coating derived upon partial or full cure of a thermosetting powder according to claim 19.

21. A substrate having coated and cured thereon a thermosetting powder according to claim 19.

* * * * *